United States Patent [19]

Sasaki et al.

[11] 4,031,215
[45] June 21, 1977

[54] STREPTOVARICINONE C DERIVATIVES AS ANTIBIOTICS

[75] Inventors: Kazuya Sasaki, Higashikurume; Takanobu Naito, Funabashi; Yoshio Momoki, Tokyo; Toshio Sega, Tokyo; Toshiyuki Satomi, Tokyo, all of Japan

[73] Assignee: Kaken Chemical Co., Ltd., Tokyo, Japan

[22] Filed: Oct. 2, 1975

[21] Appl. No.: 618,843

[30] Foreign Application Priority Data

Nov. 11, 1974 Japan .......................... 49-128967
Nov. 12, 1974 Japan .......................... 49-129523
Feb. 18, 1975 Japan .......................... 50-19470
Mar. 20, 1975 Japan .......................... 50-32953

[52] U.S. Cl. .................... 424/244; 260/239.3 P; 260/239.3 T
[51] Int. Cl.$^2$ ............ C07D 491/14; C07D 491/18; C07D 491/22
[58] Field of Search .............. 260/239.3 T, 239.3 P; 424/244

[56] References Cited
OTHER PUBLICATIONS

Rinehart et al. "J. Am. Chem. Soc.", vol. 93, No. 23, (1971) pp. 6273-6274.

Primary Examiner—Henry R. Jiles
Assistant Examiner—Robert T. Bond
Attorney, Agent, or Firm—Oblon, Fisher, Spivak, McClelland & Maier

[57] ABSTRACT

Streptovaricinone C derivatives of the formula

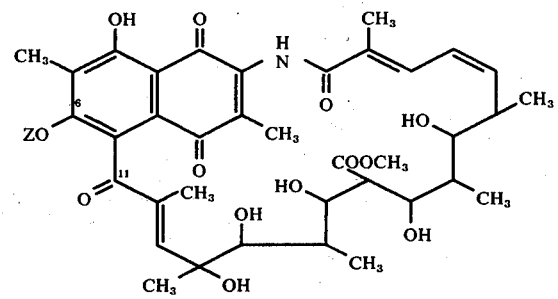

wherein Z is a $C_{1-12}$ alkyl, an aryl, a hydroxyalkyl, an alkenyl, a ketonyl, a furyl-oxoalkyl, a thienyl-oxoalkyl, a phenacyl, a carbamylalkyl, a benzyl, a phenoxyalkyl, a cyanoalkyl, a phenethyl, a benzoyloxyethyl, a p-chlorophenacyl, a p-methoxyphenacyl, a p-nitrobenzyl, a p-methylbenzyl, an alkanoyl, a benzoyl, a benzenesulfonyl, an alkylsulfonyl or an alkoxycarbonyl group, are antibiotics.

14 Claims, No Drawings

STREPTOVARICINONE C DERIVATIVES AS ANTIBIOTICS

BACKGROUND OF THE INVENTION

1. Field of the Invention

The present invention relates to novel antibiotics of streptovaricinone C derivatives.

2. Description of the Prior Art

Streptovaricins are known antibiotics produced by culturing the strain of Streptomyces 101, species 2494. The chemical formula of streptovaricins has been confirmed to be:

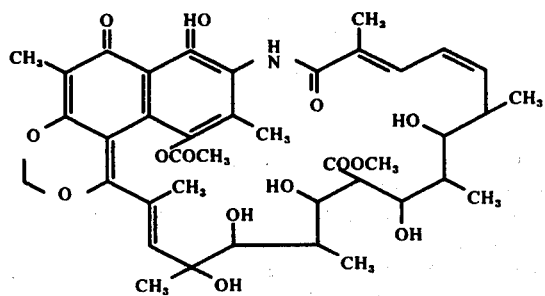

(I)

The present inventors have discovered that streptovaricin C having the formula (I) can be hydrolyzed in an alkaline medium under oxidizing conditions to produde a streptovaricinone having the formula:

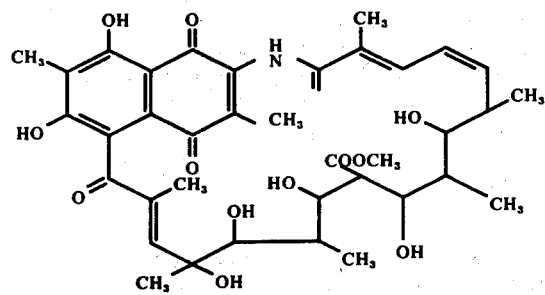

(II)

Consequently, it would be most desirable to have additional antibiotics having this new basic structure.

SUMMARY OF THE INVENTION

Accordingly, it is an object of the present invention to provide novel antibiotics which have excellent antibiotic activity.

It is another object of this invention to provide a process for producing these novel antibiotics.

Briefly, these and other objects of this invention, as will hereinafter become clear from the ensuing discussion, have been attained by providing novel antibiotics of streptovaricinone C derivatives having the formula:

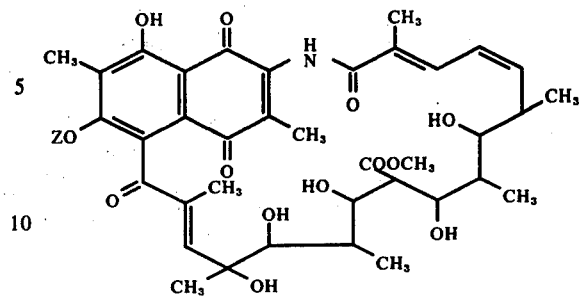

wherein Z, represents a $C_{1-12}$ alkyl, an aryl, a hydroxyalkyl, an alkenyl, a ketonyl, a furyl-oxoalkyl, a thienyloxoalkyl, a phenacyl, a carbamylalkyl, a benzyl, a phenoxyalkyl, a cyanoalkyl, a phenethyl, a benzoyloxyethyl, a p-chlorophenacyl, a p-methoxyphenacyl, a p-nitrobenzyl, a p-methylbenzyl, an alkanoyl, a benzoyl, a benzenesulfonyl, an alkylsulfonyl or an alkoxycarbonyl group.

DETAILED DESCRIPTION OF THE PREFERRED EMBODIMENTS

The streptovaricinone C derivatives of this invention can be produced by etherification or esterification of streptovaricinone C having the formula (II). The etherification of streptovaricinone C can be conducted by reacting a Z-hal (Z is the desired substituent and hal is a halogen such as Cl, Br or I) in the presence of silver oxide in a solvent such as methanol, ethanol, ether, 1,2-dimethoxyethane, tetrahydrofuran, and the like. The streptovaricinone C is dissolved and suspended in the solvent, and 0.5 – 5 mole equivalents of silver oxide are added. The mixture is stirred at room temperature for from 30 minutes to 24 hours to form a suspension of the salt, e.g., the silver salt. Excess of a halide having the formula Z is added to the suspension of the salt while stirring the reaction. The reaction can usually be conducted at room temperature for about from 30 minutes to 72 hours, whereby the hydroxyl group at the 6-position is etherified. In some cases, the hydroxyl groups at the 8-and/or 27-positions can be etherified. It is also possible to etherify the hydroxy group at the 6-position by adding a large excess of a diazoalkane in a solvent to a solution of streptovaricinone C and reacting them at room temperature.

The product can be separated and purified by conventional methods. For example, the reaction mixture can be filtered to remove the precipitate of silver halide and the filtrate then condensed and dried at 35°– 45° C under a reduced pressure. The residue is extracted by an organic solvent, washed with a dilute solution of sodium bicarbonate and purified by chromatography or recrystallization.

when acetone halide is used as the Z-hal, 6-0-acetonylstreptovaricinone C is obtained. 6-0-acetonylstreptovaricinone C can then be converted to streptovaricinone C derivatives having the formula:

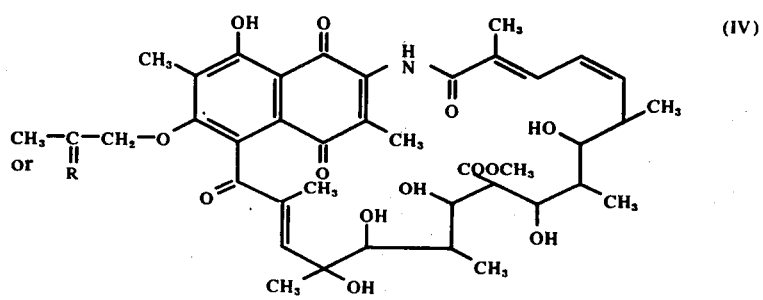

(IV)

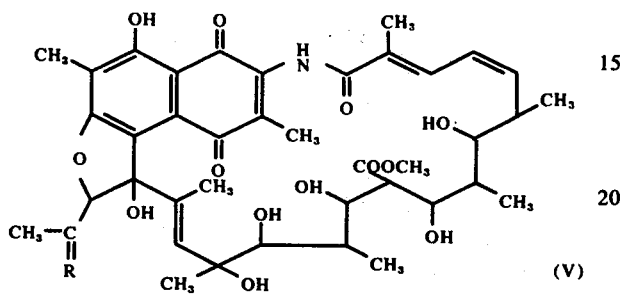

(V)

wherein R represents a hydroxyimino group, a substituted hydroxyimino group or a hydrazono group by reacting it with hydroxylamine in the presence of a strong acid.

an O-substituted hydroxylamine such as O-methylhydroxylamine, O-ethylhydroxylamine; or a substituted hydrazine such as 1-methylhydrazine, 1-ethylhydrazine, 1,1-dimethylhydrazine,1,1-diethylhydrazine, 1,1-dipropylhydrazine, 1,1-dibutylhydrazine, 1,1-dibenzylhydrazine, 1-methyl-1-phenylhydrazine, benzylidenehydrazine, cyclohexylidenehydrazine, N-aminopiperidine, N-aminomorpholine, N-amino-N'-methylpiperazine and the like, or a hydrochloride thereof.

The reaction is preferably conducted in an inert organic solvent such as benzene, methanol, tetrahydrofuran, especially in methanol under strong acidic conditions, especially using hydrochloric acid. In order to produce compound (IV), it is preferred to employ a molar ratio of the hydroxylamine or the hydrazine to 6-0-acetonylstreptovaricinone C of 1.5 – 5, at room temperature while stirring for from 3 minutes to 3 hours. The progress of the reaction can be determined by silica gel thin layer chromatography.

The products can be separated and purified by conventional methods. For example, the reaction mixture can be extracted with an organic solvent and purified by chromatography or recrystallization. In order to produce compound (VI), it is preferred to use a molar ratio of the hydroxylamine or the hydrazine to 6-0-acetonylstreptovaricinone C of about 10, especially in the presence of an excess of acetic acid, at room temperature for 0.5 – 2 hours.

6-0-ketonylstreptovaricinone C can be converted by intramolecular aldol condensation to produce a streptovaricinone C derivative having the formula:

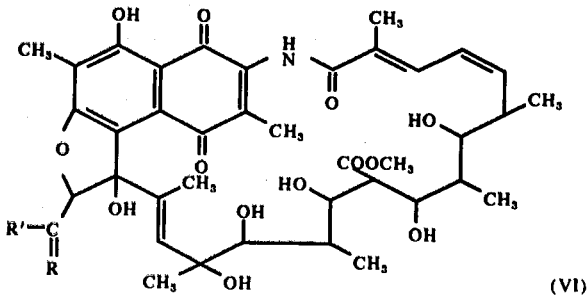

(VI)

wherein R' represents a lower alkyl group containing up to 6 carbon atoms such as a methyl or ethyl group; an aromatic residual group such as a phenyl group; a heterocyclic residual group, such as a 2-furyl group, an α-thienyl group, and substituted derivatives thereof, such as those having lower alkyl group, lower alkoxyl group, hydroxyl group, nitro group or halogen substituents.

The intramolecular aldol condensation can be conducted by adding an organic base to 6-0-ketonylstreptovaricinone C in the presence of an excess of acid in an organic solvent. The organic solvent is preferably benzene. The acid is preferably an organic acid, e.g., acetic acid. The organic base is preferably a primary amine or a secondary amine, especially benzylamine. The reaction is usually conducted at room temperature for from 0.5 to 24 hours. When benzylamine is used as the organic base, the reaction velocity is effectively high. The 6-0-ketonylstreptovaricinone C can be produced by reacting a halide having the formula R—CO—CH$_2$—hal with steptovaricinone C as described above.

The esterification of streptovaricinone C can be conducted by reacting an alkali metal salt of streptovaricinone C with an organic acyl halide, an organic sulfonyl halide or an alkyl halocarbonate. The hydroxyl group at the 6-position can be converted to a Z'0-group wherein Z' represents an alkenoyl group, a benzoyl group, a benzenesulfonyl group, an alkylsulfonyl group or an alkoxycarbonyl group which can also have inert substituents.

Suitable organic acyl halides, organic sulfonyl halides and alkyl halocarbonate include fatty acid halides, benzoil acid halides, benzenesulfonic acid halides, alkylsulfonic acid halides, methyl chlorocarbonates, and the like. The reaction is preferably conducted in an inert organic solvent such as tetrahydrofuran by adding said halide in a 1–3 molar ratio relative to the amount of alkali metal salt of streptovaricinone C while stirring at room temperature for from 5 minutes to 48 hours.

The streptovaricinone C derivatives of this invention have effective pharmacological properties, especially high antibiotic activity to Gram positive bacteria. The streptovaricinone C can be administered in the same fashion as other streptovaricin antibiotics, such as in the form of a tablet, a sugar-coated tablet, a powder, an ointment, a cream, a capsule, a solution suspension, an emulsion, and in other conventional ways. It can be administered in conjuction with a pharmaceutically acceptable carrier such as an organic or inorganic solid or liquid carrier. The dose of the streptovaricinone C derivatives of this invention should be in the range of from 100 1 mg to 3 g per day. Proper dosages can be determined using conventional considerations. Pharmacological compositions can also contain other conventional additives and pharmaceutically active ingredients.

The following tables contain the melting points and antibiotic activity of many typical streptovaricinone C derivatives. This list is not intended to be limiting in any way, but is presented for illustrative purposes only.

In vitro microbial activity:

The microbial activity was determined using standard methods according to the Japanese Chemotherapy Society. A solution of 10 mg of a drug in 1 ml of ethanol was diluted with 9 ml of 0.01% aq. Tween 80 solution, and the solution was further separately diluted with the same diluent to concentrations of 1,000, 500, 200, 100 and lower $\mu$ g/ml.

A mixture of 9 ml of warm brain heart infusion agar broth and 1 ml of the above drug solution was placed in a Petri plate and cooled to room temperature. All test organisms such as *Staphylococcus aureus* Rosenbach FDA 209 P JC-1 and *Bacilus subtilis* ATCC 6633 were incubated at 37° C for 18–20 hours in Trypto-Soy broth (Eiken) and adjusted to 1:10⁸ inoculum, except for *Mycobacterium smegmatis* ATCC 607 which was incubated at 37° C for 48 hours in brain heart infusion agar broth containing 5% glycerol.

The above bacterial solution was streaked on the Petri agar plate containing the drug and incubated at 37° C for 18–20 hours, except for *Mycobacterium smegmatis* 607 which was incubated for 48 hours at 37° C. The bacterial solution of *Mycobacterium tuberculosis* H37Rv was prepared in the homogenized Tween solution after which it was adjusted to a 0.1 mg/ml solution by turbidimetry. A mixture of 4.5 ml of Kirchner semi-liquid agar solution, 0.5 ml of horse serum and 0.5 ml of Tween solution was used for the incubation of this bacterium. One-tenth ml of said bacterial solution was seeded and incubated at 37° C for two weeks. The minimum inhibitory concentration (MIC) was the lowest concentration of the drug which prevented visible growth after incubation.

Table 1

6-O-substituted streptovaricinones C shown by the formula III

| Z | Melting point (° C) | St. aureus 209 P | Bacilus subtilis | Myco. smeg. 607 | Myco. tuberc. H37Rv |
|---|---|---|---|---|---|
| H—(Reference) | 284–285 | 50 | > 100 | > 100 | > 100 |
| 1 CH₃— | 165–167 | 1 | 10 | 20 | 10 |
| 2 CH₃CH₂— | 156–158 | 1 | 0.5 | 20 | 50 |
| 3 CH₃CH₂CH₂— | 163–164 | 10 | 5 | 5 | 20 |
| 4 CH₃CH₂CH₂CH₂— | 154–155 | 10 | 5 | 20 | 50 |
| 5 CH₃(CH₂)₄— | 148–149 | 10 | 5 | 5 | 20 |
| 6 (CH₃)₂CHCH₂CH₂— | 150–152 | 10 | 5 | 20 | 50 |
| 7 CH₃(CH₂)₅— | 131–133 | 5 | 2 | 2 | 20 |
| 8 CH₃(CH₂)₆— | 128–130 | 2 | — | 0.5 | 10 |
| 9 ClCH₂CH₂— | 156–158 | 1 | 1 | — | 20 |
| 10 ClCH₂CH₂CH₂— | 145–147 | 5 | 2 | 20 | 10 |
| 11 CH₂=CHCH₂— | 155–156 | 2 | 1 | 20 | 20 |
| 12 HOCH₂CH₂CH₂— | 140–141 | 5 | 5 | 0.5 | 20 |
| 13 Ph—O—CH₂CH₂— | 142–144 | 2 | — | 0.5 | 5 |
| 14 NC—CH₂CH₂CH₂— | 158–160 | 10 | 20 | 5 | 10 |
| 15 CH₃COCH₂— | 162–163 | 1 | 2 | — | 10 |
| 16 PhCOCH₂— | 144–146 | 5 | 20 | 20 | 20 |
| 17 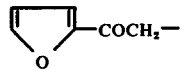 | 163–165 | 0.5 | — | 20 | 10 |
| 18 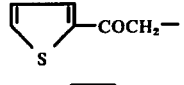 | 162–165 | 5 | — | 10 | 5 |
| 19  | 154–156 | 10 | — | 2 | 20 |
| 20 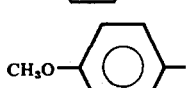 | 153–155 | 5 | 5 | 5 | 10 |
| 21 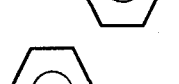 | 155–156 | 2 | — | 0.5 | 5 |
| 22 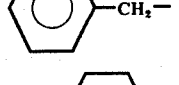 | 136–138 | 5 | — | 0.5 | 2 |

Table 1-continued
6-O-substituted streptovaricinones C shown by the formula III
| Z | Melting point (°C) | St. aureus 209 P | Bacilus subtilis | Myco. smeg. 607 | Myco. tuberc. H37Rv |
|---|---|---|---|---|---|
| 23  | 162–164 | 5 | — | 1 | 5 |
| 24 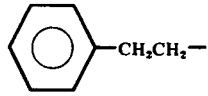 | 144–146 | 10 | 5 | 10 | 20 |
| 25 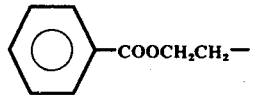 | 145–147 | 5 | — | 1 | 50 |
| 26 $CH_3CO-$ | 169–171 | 20 | — | — | 5 |
| 27 $CH_3CH_2CO-$ | 160–162 | 10 | — | — | 20 |
| 28 $CH_3CH_2CH_2CO-$ | 156–157 | 20 | — | — | 5 |
| 29 $CH_3(CH_2)_3CO-$ | 153–156 | 2 | — | — | 5 |
| 30 $CH_3(CH_2)_4CO-$ | 144–147 | 2–5 | — | — | 10 |
| 31 $Br-CH_2CO-$ | 165–168 | 10 | — | — | 5 |
| 32 $PhCH_2CO-$ | 154–155 | 20 | — | — | 5 |
| 33 $CH_3(CH_2)_3S-CH_2CO-$ | 132–134 | 5 | — | — | 0.5 |
| 34 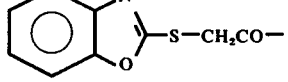 | 150–153 | 10 | — | — | 1 |
| 35 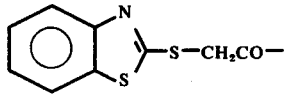 | 139–142 | 10 | — | — | 1 |
| 36 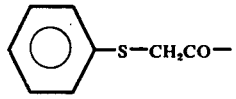 | 142–144 | 10 | — | — | 0.5 |
| 37 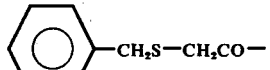 | 134–136 | 5 | — | — | 1 |
| 38 $CH_3SO_2-$ | 167–170 | 1 | — | — | 2 |
| 39 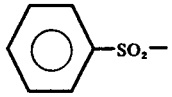 | 156–158 | 2 | — | — | 5 |
| 40  | 162–165 | 1 | — | — | 1 |
| 41 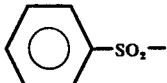 | 165–167 | 5 | — | — | 2 |
| 42  | 180–184 | 5 | — | — | 2 |
| 43 $CH_3O-CO-$ | 160–163 | 2 | — | — | 10 |
| 44 $CH_3CH_2O-CO-$ | 152–154 | 2 | — | — | 1 |
| 45 $(CH_3)_2CHCH_2OCO-$ | 150–152 | 0.2 | — | — | 5 |
| 46 $CH_3(CH_2)_3OCO-$ | 138–141 | 1 | — | — | 1 |
| 47 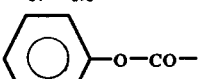 | 164–165 | 5 | — | — | 1 |
| 48 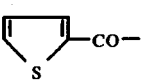 | 186–188 | 5 | — | — | 1 |

TABLE 2

6-O-substituted streptovaricinones C, shown by the formula IV:

| | R | Melting point (°C) | St. aureus 209P | Bacilus subtilis | Myco. smeg. 607 | Myco. tuberc. H37Rv |
|---|---|---|---|---|---|---|
| 49 | =N—O—H | 166–167 | 0.2 | 100 | 20 | 5 |
| 50 | =N—O—CH₃ | 145–147 | 0.5 | 0.5 | 50 | 20 |
| 51 | =N—O—C₂H₅ | 142–144 | 0.5 | — | — | 5 |
| 52 | =N—O—n-C₃H₇ | 138–140 | 5 | — | — | 20 |
| 53 | =N—O—n-C₄H₉ | 130–132 | 2 | — | — | 2 |
| 54 | =N—O—n-C₅H₁₁ | 129–132 | 1 | — | — | 2 |
| 55 | =N—O—n-C₆H₁₃ | 124–126 | 2 | — | — | 10 |
| 56 | =N—O—n-C₉H₁₉ | 106–109 | 10 | — | — | 5 |
| 57 | =N—O—CH₂CH=CH₂ | 132–134 | 2 | — | — | 20 |
| 58 | =N—O—CH₂Ph | 144–145 | 2 | — | — | 10 |
| 59 | =N—O—CH₂CH₂OOCPh | 110–113 | 0.5 | — | — | 2 |
| 60 | =N—O—CH₂CH₂O—Ph | 106–109 | 0.5 | — | — | 2 |
| 61 | =N—NH—CONH₂ | 236–237 | 0.5 | 0.5 | 50 | 20 |
| 62 | =N—NH—CO—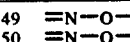 | 182–183 | 1 | 1 | 20 | 10 |

Table 3

6-O-substitute streptovaricinones C, shown by the formula V:

| | R | Melting point (°C) | St. aureus 209P | Bacilus subtilis | Myco smeg. 607 | Myco tuberc. H37Rv |
|---|---|---|---|---|---|---|
| 63 | =N—O—H | 189–190 | 0.2 | 100 | 20 | 5 |
| 64 | =N—NHMe | 170–171 | 0.2 | — | — | 10 |
| 65 | =N—N(Me)₂ | 166–167 | 0.2 | 100 | 50 | 20 |
| 66 | =N—NH—CH₂CH₂OH | 170–171 | 0.2 | — | — | 20 |
| 67 | =N—N(n-C₃H₇)₂ | 154–155 | 0.2 | — | 10 | 20 |
| 68 | =N—N(n-C₄H₉)₂ | 140–141 | 0.2 | — | 50 | 20 |
| 69 | =N—N(n-C₅H₁₁)₂ | 132–133 | <0.1 | — | 10 | 20 |
| 70 | =N—N(n-C₆H₁₃)₂ | 122–123 | 2 | — | — | > 50 |
| 71 | =N—N(n-C₈H₁₇)₂ | 97–98 | 1 | — | — | > 50 |
| 72 | =N—N(CH₂CH=CH₂)₂ | 148–149 | 1 | — | — | 20 |
| 73 | =N—N(Me)Ph | 156–157 | 5 | — | > 50 | > 100 |
| 74 | =N—N(Et)Ph | 153–154 | 2 | — | > 100 | > 100 |
| 75 | =N—N=CHPh | 166–167 | 0.2 | — | > 100 | 50 |
| 76 | =N—N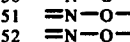N—Me | 174–175 | 1 | — | 20 | 20 |
| 77 | =N—N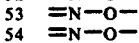O | 173–174 | 2 | — | 50 | 20 |
| 78 | =N—N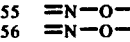 | 165–166 | 0.5 | — | 20 | 20 |
| 79 | =N—N | 170–171 | 0.5 | 0.5 | 50 | 20 |
| 80 | =N—N | 162–163 | 0.5 | — | 20 | 20 |
| 81 | =N—N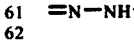 | 184–185 | 0.2 | — | 20 | 20 |
| 82 | =N—N—CH₃ | 167–170 | < 0.1 | — | 20 | 20 |
| 83 | =N—NCH₃ | 167–168 | 0.2 | — | 20 | 20 |

Table 3-continued

6-O-substitute streptovaricinones C, shown by the formula V:

| R | Melting point (° C) | St. aureus 209P | Bacilus subtilis | Myco. smeg. 607 | Myco. tuberc. H37Rv |
|---|---|---|---|---|---|
| 84 =N—N(piperidine with CH₃) | 170–171 | 0.2 | — | 20 | 20 |

Table 4

6-O-substituted streptovaricinones C, shown by the formula VI:

| R' | Melting point (° C) | St. aureus 209P | Bacilus subtilis | Myco. smeg. 607 | Myco. tuberc. H37Rv |
|---|---|---|---|---|---|
| 85 $CH_3-$ | 162–163 | 0.2 | 0.5 | 50 | 100 |
| 86 $CH_3CH_2-$ | 161–163 | 10 | — | — | 10 |
| 87 phenyl- | 164–166 | 2 | 2 | — | 50 |
| 88 4-Cl-phenyl- | 159–162 | 10 | — | — | 10 |
| 89 4-MeO-phenyl- | 162–165 | 5 | — | — | 10 |
| 90 furyl- | 163–165 | 2 | — | — | 20 |
| 91 thienyl- | 168–170 | 5 | — | — | 10 |

Having generally described the invention, a more complete understanding can be obtained by reference to certain specific Examples, which are provided herein for purposes of illustration only and are not intended to be limiting unless otherwise specified.

EXAMPLE 1

Preparation of 6-0-methylstreptovaricinone C

To a suspension of 1.42 g of streptovaricinone C in 70 ml of methanol was added 400 mg of silver oxide, and the mixture was stirred at room temperature for 1 hour. To the resultant mixture was added 3 g of methyl iodide, and the reaction mixture was stirred at room temperature for 1 hour and filtered through Celite. The filtrate was evaporated under reduced pressure to dryness to give a red oil. The oil was recrystallized from acetone-n-hexane as yellow needles, m.p. 165°–167° C, affording a single spot on silica gel t.l.c. The yield was 860 mg.

EXAMPLE 2

Preparation of 23,24-dihydro-6-0-methylstreptovaricinone C

To a suspension of 50 mg of streptovaricinone C in 5 ml of tetrahydrofuran was added 20 ml of diazomethane-ether solution while cooling in an ice-water bath for 30 minutes. Thereafter, a few drops of acetic acid were added. The reaction mixture was evaporated to dryness under reduced pressure, and the residue was dissolved in a small amount of ethyl acetate. To the solution was added a large amount of n-hexane to give a yellow precipitate which was recrystallized from acetone-n-hexane to yield 25 mg of 6-0-methylstreptovaricinone C, melting at 165°–167° C. The product showed the same Rf value as the one obtained in Example 1 on silica gel t.l.c.

EXAMPLE 3

Preparation of 23,24-dihydro-6-0-methylstreptovaricinone C

To a solution of 50 mg of 23,24-dihydrostreptovaricinone C in 3 ml of methanol was added 17 mg of silver oxide while stirring at room temperature for 30 minutes. To the resultant mixture was added 1 ml of methyl iodide, and the reaction mixture was stirred at room temperature for 30 minutes, and then filtered. The filtrate was evaporated under reduced pressure to give a red oil. The oil was chromatographed on Sephadex LH-20 with acetone, and the appropriate fractions were collected and evaporated to dryness under reduced pressure. The resulting oil was recrystallized from chloroform-n-hexane to yield 31 mg of yellow crystalline powder, melting at 135°–137° C.

EXAMPLE 4

Preparation of 6-0-phenacylstreptovaricinone C

To a suspension of 713 mg of streptovaricinone C in 80 ml of methanol was added 1.16 g of silver oxide, and the mixture was stirred at 20° C for 2 hours. To the resulting mixture was added 2 g of -bromo-acetophenone, and the reaction mixture was stirred at room temperature for 18 hours, and filtered through Celite. The filtrate was evaporated to dryness under reduced pressure to give a red oil. The oil was chromatographed on Sephadex LH-20 with acetone, and the appropriate fractions were collected, and evaporated to dryness under reduced pressure. The resulting oil was recrystallized from acetone-n-hexane to afford 338 mg of yellow needles of 6-0-phenacylstreptovaricinone C, m.p. 155°–157° C.

EXAMPLE 5

Preparation of 6-0-cyclohexylstreptovaricinone C

To a suspension of 570 mg of streptovaricinone C in 50 ml of methanol was added 928 mg of silver oxide, and the mixture was stirred at 25° C for 3 hours. To the resultant mixture was added 3.26 g of cyclohexyl bromide. The reaction mixture was stirred at 25° C for 18 hours and then 928 mg more of silver oxide was added and the mixture was stirred at 50° C for 10 minutes. To the mixture was added 3.26 g more of cyclohexyl bromide, and stirring extended for 1 hour at room temperature. The mixture was then filtered, and the filtrate was evaporated to dryness under reduced pressure. The resulting oil was dissolved in 150 ml of ethyl acetate, and the solution was washed with 5% sodium bicarbonate solution. The organic layer was separated, and evaporated to dryness under reduced pressure to give a red oil which was chromatographed on silica gel with 3% methanol in chloroform. The appropriate fractions were collected and evaporated to dryness under reduced pressure to give a red oil which was recrystallized from chloroform-n-hexane as 185 mg of 6-0-cyclohexylstreptovaricinone C, m.p. 164°–165° C.

EXAMPLE 6

Preparation of 6-0-(3'-chloro-propyl)streptovaricinone C

To a suspension of 120 mg of streptovaricinone C in 10 ml of methanol was added 120 mg of silver oxide, and the mixture was stirred at room temperature for 1 hour. Then, to the mixture was added 1.5 g of 1-chloro-3-bromopropane, and the reaction mixture was stirred at room temperature for 40 hours. The reaction mixture was then filtered through Celite, and the filtrate was evaporated to dryness under reduced pressure. The residue was chromatographed on silica gel with 4% methanol in chloroform, and the appropriate fractions were collected, and evaporated to dryness under reduced pressure to give a red oil which was recrystallized from chloroform-n-hexane as 20 mg of yellow crystalline powder of 6-0-(3'-chloropropyl)streptovaricinone C, m.p. 145°–147° C.

EXAMPLE 7

Preparation of the aldol compound of 6-0-acetonyl-streptovaricinone C

To a solution of 2.70 g of 6-0-acetonylstreptovaricinone C in a mixed solution of 70 ml of benzene and 14 ml of acetic acid was added 3.74 g of benzylamine. The reaction mixture was stirred at room temperature for 30 minutes, and then diluted with 200 ml of benzene. The solution was washed with water three times, dried over anhydrous sodium sulfate, and evaporated to dryness under reduced pressure to give a red oil. The oil was chromatographed on silica gel with 3% methanol in chloroform, and the appropriate fractions collected. After the combined fraction was evaporated to dryness under reduced pressure, the residue was recrystallized from ethyl acetate-n-hexane to afford 2.05 g of orange crystalline powder of the aldol of 6-0-acetonylstreptovaricinone C, m.p. 162°–163° C.

EXAMPLE 8

Preparation of the aldol compound of 6-0-phenacylstreptovaricinone C

To a solution of 208 mg of 6-0-phenacylstreptovaricinone C in a mixed solution of 10 ml of benzene and 2 ml of acetic acid was added 200 mg of piperidine, and the reaction mixture was stirred at room temperature for 20 hours. The solution was then diluted with 100 ml of ethyl acetate. The solution was washed with water three times followed by a saline solution, dried over anhydrous sodium sulfate, and evaporated to dryness under reduced pressure. The resulting red oil was recrystallized from chloroform-n-hexane to afford 120 mg of orange red crystalline powder of the aldol compound of 6-0-phenacylstreptovaricinone C, m.p. 164°–166° C.

EXAMPLE 9

Preparation of the oxime of the aldol compound from 6-0-acetonylstreptovaricinone C (Method A)

To a solution of 385 mg of 6-0-acetonylstreptovaricinone C in 10 ml of benzene was added 330 mg of hydroxylamine and 2 ml of acetic acid in 5 ml of benzene, and the mixture was stirred at room temperature for 30 minutes. The resulting mixture was evaporated to dryness under reduced pressure, and the residue was chromatographed on silica gel with 10% methanol in chloroform. The appropriate fractions were collected, combined, and evaporated to dryness under reduced pressure to give a red oil which was recrystallized from ethyl acetate-n-hexane as 161 mg of orange yellow crystals of the product, m.p. 189°–190° C.

EXAMPLE 10

Preparation of the oxime of the aldol compound of 6-0-acetonylstreptovaricinone C (Method B)

To a solution of 385 mg of the aldol compound of 6-0-acetonylstreptovaricinone C in 10 ml of methanol was added 347 mg of hydroxylamine hydrochloride, and the mixture was stirred at room temperature for 1.5 hour. The resulting mixture was diluted with 40 ml of ethyl acetate, and the solution was washed with aqueous sodium bicarbonate solution three times, dried over anhydrous sodium sulfate, and evaporated to dryness under reduced pressure to give a red oil. The oil was chromatographed on silica gel with 5% methanol in chloroform, and the appropriate fractions were collected, combined, and evaporated to dryness under reduced pressure to furnish a red oil which was recrystallized from ethyl acetate-n-hexane as 249 mg of the product, m.p. 189°–190° C. The product showed the same Rf value on t.l.c., IR spectrum (KBr), and melting point as those of the one obtained in Example 1.

EXAMPLE 11

Preparation of the N,N-dimethylhydrazone of aldol compound of 6-0-acetonylstreptovaricinone C To a solution of 385 mg of the aldol compound of 6-0-acetonylstreptovaricinone C in 10 ml of benzene was added 30 mg of N,N-dimethylhydrazine hydrochloride, and the mixture was stirred at room temperature for 1 hour. The mixture was then diluted with 30 ml of benzene. The mixture was washed with water twice, dried over anhydrous sodium sulfate, and evaporated to dryness under reduced pressure to give a red oil. The oil was chromatographed on Sephadex LH-20 with methanol, and the appropriate fractions were collected, combined, and evaporated to dryness to furnish a red oil which was recrystallized from ethyl acetate-n-hexane to afford 110 mg of yellow crystalline powder of the product, m.p. 166°–167° C.

EXAMPLE 12

Preparation of N,N-di-n-pentylhydrazone of the aldol compound of 6-0-streptovaricinone C To a solution of 385 mg of 6-0-acetonylstreptovaricinone C in 10 ml of benzene was added 860 mg of 1,1-di-n-pentylhydrazine and 2 ml of acetic acid, and the mixture was stirred at room temperature for 30 minutes. The resultant reaction mixture was diluted with 30 ml of benzene, washed with water three times, dried over anhydrous sodium sulfate, and evaporated to dryness under reduced pressure to give a red oil. The oil was chromatographed on Sephadex LH-20 with acetone, and the appropriate fractions were collected, combined, and evaporated to dryness to afford an oil. The oil was recrystallized from ethyl acetate-n-hexane as 230 mg of N,N-di-n-pentylhydrazone of the aldol compound of 6-0-acetonylstreptovaricinone C, m.p. 132°–133° C.

EXAMPLE 13

Preparation of 6-0-acetonylstreptovaricinone C O-n-butyloxime

To a solution of 200 mg of 6-0-acetonylstreptovaricinone C in 10 ml of methanol was added 125 mg of 0-n-butylhydroxylamine hydrochloride, and the mixture was stirred at room temperature for 2 hours. The resultant mixture was diluted with 200 ml of ethyl acetate and the solution was washed with water, dried over anhydrous sodium sulfate, and evaporated to dryness under reduced pressure to give an orange oil which was recrystallized from acetone-n-hexane to afford 146 mg of yellow needles of the O-n-butyloxime, m.p. 130°–132° C.

EXAMPLE 14

Preparation of 6-0-acetonylstreptovaricinone C 0-benzyloxime

To a solution of 256 mg of 6-0-acetonylstreptovaricinone C in 15 ml of methanol was added 100 mg of 0-benzylhydroxylamine hydrochloride, and the reaction mixture was stirred at room temperature for 45 minutes. The resultant mixture was diluted with 200 ml of ethyl acetate, washed with water repeatedly, dried over anhydrous sodium sulfate, and evaporated to dryness under reduced pressure to give a red oil. The oil was chromatographed on silica gel with 4% methanol in chloroform, and the appropriate fractions were collected, combined, and evaporated to dryness to give an orange oil which was recrystallized from acetone-n-hexane to afford 198 mg of yellow needles of the O-benzyloxime, m.p. 144°–145° C.

EXAMPLE 15

Preparation of 6-0-acetonylstreptovaricinone C semicarbazone

To a solution of 231 mg of 6-0-acetonylstreptovaricinone C in 15 ml of methanol was added 45 mg of semicarbazide hydrochloride, and the reaction mixture was stirred at room temperature for 30 minutes. The resultant mixture was evaporated to dryness under reduced pressure, and the resulting oil was chromatographed on silica gel with 10% methanol in chloroform. The appropriate fractions were collected, combined, and evaporated to dryness under reduced pressure to give an orange oil which was recrystallized from ethyl acetate-n-hexane as 115 mg of yellow crystalline powder of 6-0-acetonylstreptovaricinone C semicarbazone, m.p. 235°–236° C.

EXAMPLE 16

Preparation of 6-0-acetylstreptovaricinone C

To a suspension of 363 mg of streptovaricinone C in 10 ml of acetone was added 10 ml of 0.05 N methanolic sodium hydroxide solution, and the solution was evaporated to dryness under reduced pressure to obtain a sodium salt of streptovaricinone C. The sodium salt was suspended in 20 ml of dry tetrahydrofuran, and to the suspension was added 90 mg of acetyl chloride. The reaction mixture was stirred at room temperature for 5 minutes, and then poured into 5% cold sodium bicarbonate solution. The mixture was extracted with benzene repeatedly, and the combined extract was washed with water, dried over anhydrous sodium sulfate, and evaporated to dryness under reduced pressure to give a red oil. The oil was chromatographed on silica gel with 5% methanol in chloroform, and the appropriate fractions were collected and combined. The fraction was evaporated to dryness under reduced pressure to afford an orange oil which was recrystallized from acetone-n-hexane as 182 mg of 6-0-acetylstreptovaricinone C, m.p. 169°–171° C.

EXAMPLE 17

Preparation of 6-0-(3',5'-dinitrobenzoyl)-streptovaricinone C

To a suspension of 360 mg of streptovaricinone C in 30 ml of methanol was added 10 ml of 0.05N methanolic sodium hydroxide solution, and the mixture was stirred for 15 minutes and evaporated to dryness under reduced pressure to form the sodium salt. The sodium salt was then suspended in 10 ml of dry tetrahydrofuran, and to the suspension was added 116 mg of 3,5-dinitrobenzoyl chloride, and the mixture was stirred at room temperature for 30 minutes, and evaporated to dryness under reduced pressure. The residue was dissolved in ethyl acetate, and the solution was washed with water, dried over anhydrous sodium sulfate, and evaporated to dryness under reduced pressure. The residue was chromatographed on Sephadex LH-20 with acetone, and the appropriate fractions were collected and combined. The fraction was evaporated to dryness under reduced pressure to give an orange red oil which was recrystallized from chloroform-n-hexane to afford a yellow crystalline powder of 6-0-(3',5'-dinitrobenzoyl)streptovaricinone C, m.p. 178°–182° C.

EXAMPLE 18

Preparation of 6-0-methanesulfonylstreptovaricinone C

To a suspension of 372 mg of streptovaricinone C in 10 ml of acetone was added 10 ml of 0.05N methanolic sodium hydroxide solution, and the solution was evaporated to dryness under reduced pressure to obtain the sodium salt of streptovaricinone C. The sodium salt was suspended in 20 ml of dry tetrahydrofuran, and to the suspension was added 138 mg of methanesulfonyl chloride in 10 ml of dry tetrahydrofuran, and the reaction mixture was stirred at room temperature for 48 hours, and then poured into 5% cold sodium bicarbonate solution. The mixture was extracted with ethyl acetate, and the extract was washed with water, dried over anhydrous sodium sulfate, and evaporated to dryness to give a red oil. The oil was chromatographed on silica gel with 4% methanol in chloroform, and the appropriate fractions were collected, and combined. The fraction was evaporated to dryness under reduced pressure to afford an orange oil which was recrystallized from ethyl acetate-n-hexane to give 57 mg of yellow crystalline powder of 6-0-methanesulfonylstreptovaricinone C, m.p. 167°–170° C.

EXAMPLE 19

Preparation of 6-0-methoxycarbonylstreptovaricinone C

To a suspension of 373 mg of streptovaricinone C in 10 ml of tetrahydrofuran was added 10 ml of 0.05N methanolic sodium hydroxide solution, and the solution was evaporated to dryness under reduced pressure to obtain the sodium salt of streptovaricinone C. The salt was suspended in 8 ml of tetrahydrofuran, and to the suspension was added 145 mg of methyl chlorocarbonate. The reaction mixture was stirred at room temperature for 30 minutes, and poured into 5% cold sodium bicarbonate solution. The mixture was then extracted with ethyl acetate repeatedly, and the extract was washed with water, dried over anhydrous sodium sulfate, and evaporated to dryness under reduced pressure to give a red oil. The oil was chromatographed on silica gel with 7% methanol in chloroform, and then the appropriate fractions were collected and combined. The fraction was evaporated to dryness under reduced pressure to afford an oil which was recrystallized from ethyl acetate-n-hexane to give 263 mg of a yellow crystalline powder of 6-0-methoxycarbonylstreptovaricinon C, m.p. 159°–163° C.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A streptovaricinone C derivative of the formula:

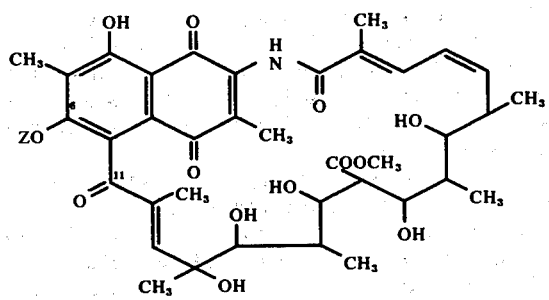

wherein Z is alkyl, a phenyl or a phenyl substituted by a halogen, an alkoxy group, an alkyl group or $NO_2$, a hydroxyalkyl, an alkenyl, a ketonyl having the formula

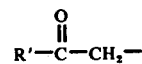

wherein R' is a lower alkyl group containing up to 6 carbon atoms, a phenyl group, a 2-furyl group, an α-thienyl group, and substituted derivatives thereof, wherein the substituent is a $C_1$-$C_6$ alkyl group, a $C_1$-$C_6$ alkoxy group, an hydroxyl group, a nitro group or a halogen, a furyl-oxoalkyl, a thienyl-oxoalkyl, a phenacyl, a carbamylalkyl, a benzyl, a phenoxyadkyl, a cyanoalkyl, a phenethyl, a benzoyloxyethyl, a p-chlorophenacyl, a p-methoxyphenacyl, a p-nitrobenzyl, a p-methylbenzyl, an alkanoyl, a benzoyl, a benzenesulfonyl, an alkylsulfonyl or an alkoxy-carbonyl group wherein alkyl, alkoxy, alkenyl, alkanoyl and alkoxycarbonyl have 1-12 carbon atoms unless otherwise specified.

2. The streptovaricinone C derivatives of claim 1, wherein Z is

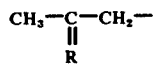

and R is hydroxyimino, hydroxyimino wherein O is substituted with a $C_{1-9}$ alkyl group, allyl, benzyl, $-CH_2CH_2OOC-C_6H_5$ or $-CH_2CH_2-O-C_6H_5$, hydrazono or a hydrazono, $=N-NR''R'''$, wherein R'' and R''' are the same or different and each is $C_{1-8}$ alkyl, benzyl, phenyl, benzylidene, cyclohexylidene, allyl or amido, or NR''R''' together forms a piperazine ring, a morpholine ring, a piperidine ring or a methyl derivative thereof, a pyrrolidine ring,

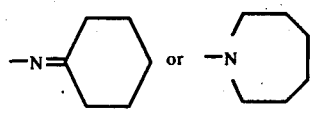

3. The streptovaricinone C derivatives of claim 1, wherein Z is an alkanoyl, a benzoyl, a benzenesulfonyl, an alkylsulfonyl, an alkoxycarbonyl group, or derivatives thereof having inert substituents selected from the group consisting of halo, alkoxy or $NO_2$.

4. A process for producing a streptovaricinone C derivative of claim 1 which comprises etherifying the 6-position of streptovaricinone C with a halide of the desired etherifying group in the presence of silver oxide in an inert solvent 5. A process for producing a streptovaricinone C derivative of claim 1 which comprises esterifying the 6-position of an alkali metal salt of streptovaricinone C with an organic acid halide, an organic sulfonic acid halide or an alkyl halocarbonate which reactants provide the ester group Z.

6. A process for producing a streptovaricinone C derivative of claim 2 which comprises
    effecting the etherification process of claim 4 wherein said halide is acetone halide; and
    then reacting the 6-0-acetonylstreptovariconone C product of said etherification with hydroxylamine, an O-substituted hydroxylamine or hydrazine or a substituted hydrazine, which reactants provide the substituent R.

7. An aldol condensation product of the streptovaricinone C derivative of claim 1 having the formula:

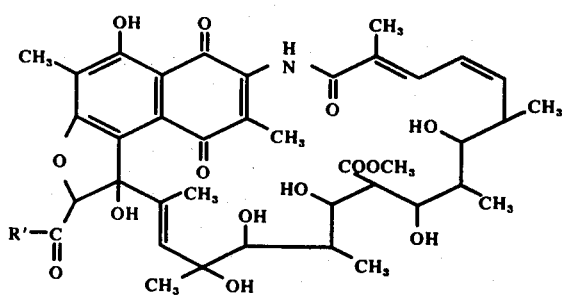

wherein R' is a lower alkyl group containing up to 6 carbon atoms, a phenyl group, a 2-furyl group, an α-thienyl group, and substituted derivatives thereof, wherein the substituent is a $C_1$-$C_6$ alkyl group, a $C_1$-$C_6$ alkoxy group, an hydroxyl group, a nitro group or a halogen.

8. The aldol condensation product of claim 7 wherein R' is $CH_3$.

9. An aldol condensation product of the streptovaricinone C derivative of claim 1 having the formula:

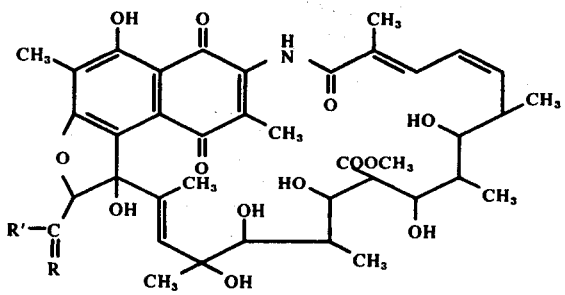

wherein R' is a lower alkyl group containing up to 6 carbon atoms, a phenyl group, a 2-furyl group, an α-thienyl group, and substituted derivatives thereof wherein the substituent is a $C_1$-$C_6$ alkoxy group, an hydroxyl group, a nitro group or a halogen, and R is hydroxyimino, hydroxyimino wherein O is substituted with a $C_{1-9}$ alkyl group, allyl, benzyl, —$CH_2C$-$H_2OOC$—$C_6H_5$ or —$CH_2CH_2$—O—$C_6H_5$, hydrazono or a hydrazono, =N—NR'' R''', wherein R'' and R''' are the same or different and each is $C_{1-8}$ alkyl, benzyl, phenyl, benzylidene, cyclohexylidene, allyl or amido, or NR'' R''' together forms a piperazine ring, a morpholine ring, a piperidine ring or a methyl derivative thereof, a pyrrolidine ring,

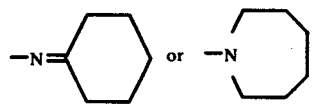

10. The aldol condensation product of claim 9 wherein R' is $CH_3$.

11. A pharmaceutical composition which comprises an antibiotically effective amount of a streptovaricinone C derivative of claim 1 and a pharmaceutically acceptable carrier.

12. A pharmaceutical composition which comprises an antibiotically effective amount of a streptovaricinone C derivative of claim 7 and a pharmaceutically acceptable carrier.

13. A pharmaceutical composition which comprises an antibiotically effective amount of a streptovaricinone C derivative of claim 9 and a pharmaceutically acceptable carrier.

14. A pharmaceutical composition which comprises an antibiotically effective amount of a streptovaricinone C derivative of claim 2 and a pharmaceutically acceptable carrier.

* * * * *

UNITED STATES PATENT AND TRADEMARK OFFICE
CERTIFICATE OF CORRECTION

PATENT NO. : 4,031,215
DATED : June 21, 1977
INVENTOR(S) : Sasaki et al

It is certified that error appears in the above-identified patent and that said Letters Patent are hereby corrected as shown below:

Column 1, lines 17 to 30, change " 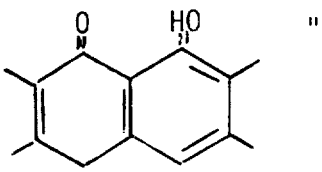 "

to --  --.

Column 1, line 36, change "dude" to --duce--.

Column 1, line 36, after "streptovaricinone" and before "having" insert --C--.

(continued)

UNITED STATES PATENT AND TRADEMARK OFFICE
CERTIFICATE OF CORRECTION

PATENT NO. : 4,031,215

DATED : June 21, 1977

INVENTOR(S) : Sasaki et al

It is certified that error appears in the above-identified patent and that said Letters Patent are hereby corrected as shown below:

Column 1, lines 36 to 50, change " 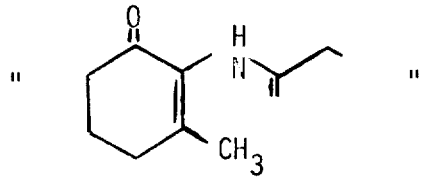 "

to -- 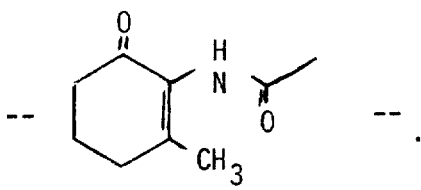 --.

Column 2, line 54, delete "at room temperature" and insert --with cooling--.

Column 2, line 64, delete "when" and insert --When--.

Column 2, line 65, change "acetonylstreptovaricinone" (both occurrences) to --Acetonylstreptovaricinone--.

Column 3, line 28, delete "an" and insert --An--.

Column 3, line 57, change "ketonylstreptovaricinone" to (continued)

UNITED STATES PATENT AND TRADEMARK OFFICE
CERTIFICATE OF CORRECTION

PATENT NO. : 4,031,215

DATED : June 21, 1977

INVENTOR(S) : Sasaki et al

It is certified that error appears in the above-identified patent and that said Letters Patent are hereby corrected as shown below:

--Ketonylstreptovaricinone--.

Column 4, line 54, change "alkenoyl" to --alkanoyl--.

Column 4, line 60, change "benzoil" to --benzoic--.

Column 5, line 9, after "100" and before "mg", delete --1--.

Column 11, lines 63 and 64, delete --23, 24-hihydro- --.

Column 13, line 7, before "-bromo-acetophe-" insert --α--.

Signed and Sealed this

Thirteenth Day of December 1977

[SEAL]

Attest:

RUTH C. MASON
Attesting Officer

LUTRELLE F. PARKER
Acting Commissioner of Patents and Trademarks